United States Patent
Betzold

(10) Patent No.: US 8,046,063 B2
(45) Date of Patent: Oct. 25, 2011

(54) IMPLANTABLE MEDICAL DEVICE WITH ADAPTIVE OPERATION

(75) Inventor: Robert A. Betzold, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 1256 days.

(21) Appl. No.: 11/364,290

(22) Filed: Feb. 28, 2006

(65) Prior Publication Data

US 2007/0203523 A1    Aug. 30, 2007

(51) Int. Cl.
*A61N 1/00* (2006.01)
*A61B 5/05* (2006.01)

(52) U.S. Cl. .......... 607/9; 607/14; 607/17; 607/25; 607/27; 607/28; 600/547

(58) Field of Classification Search ............ 600/547; 607/9, 14, 17, 25, 27, 28
See application file for complete search history.

(56) References Cited

U.S. PATENT DOCUMENTS

| | | |
|---|---|---|
| 3,057,356 A | 10/1962 | Greatbatch |
| 3,253,596 A | 5/1966 | Keller |
| 3,478,746 A | 11/1969 | Breatbatch |
| 3,595,242 A | 7/1971 | Berkovits |
| 3,648,707 A | 3/1972 | Greatbatch |
| 3,747,604 A | 7/1973 | Berkovits |
| 4,312,355 A | 1/1982 | Funke |
| 4,386,610 A | 6/1983 | Leckrone |
| 4,428,378 A | 1/1984 | Anderson et al. |
| 4,432,362 A | 2/1984 | Leckrone et al. |
| 4,476,868 A | 10/1984 | Thompson |
| 4,523,593 A | 6/1985 | Rueter et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallok |
| 4,856,523 A | 8/1989 | Sholder et al. |
| 4,856,524 A | 8/1989 | Baker |
| 4,880,005 A | 11/1989 | Pless et al. |
| 4,890,617 A | 1/1990 | Markowitz et al. |
| 4,932,046 A | 6/1990 | Katz et al. |
| 4,941,471 A | 7/1990 | Mehra |
| 4,953,551 A | 9/1990 | Mehra et al. |

(Continued)

FOREIGN PATENT DOCUMENTS

EP    0363015    4/1990

(Continued)

OTHER PUBLICATIONS

"INTRINSIC™/INTRINSIC™ 30, 7288/7287 Reference Manual", May 24, 2004, 9 pgs.

*Primary Examiner* — Niketa Patel
*Assistant Examiner* — Nicole F Lavert
(74) *Attorney, Agent, or Firm* — Reed Duthler; Stephen W. Bauer

(57) ABSTRACT

An implantable medical device operates with an algorithm that promotes intrinsic conduction and reduces ventricular pacing. The IMD monitors the occurrence of necessary ventricular pacing and takes certain actions based upon whether this occurrence has been relatively high or relatively low. When noise is detected, asynchronous pacing is provided when the occurrence is relatively high and is not provided when relatively low. When atrial threshold testing is performed, the incidence will determine which methodology is utilized.

11 Claims, 4 Drawing Sheets

U.S. PATENT DOCUMENTS

| | | | |
|---|---|---|---|
| 5,052,388 A | 10/1991 | Sivula et al. | |
| 5,085,215 A | 2/1992 | Nappholz et al. | |
| 5,097,832 A | 3/1992 | Buchanan | |
| 5,117,824 A | 6/1992 | Keimel et al. | |
| 5,133,350 A | 7/1992 | Duffin | |
| 5,144,950 A | 9/1992 | Stoop et al. | |
| 5,163,427 A | 11/1992 | Keimel | |
| 5,188,105 A | 2/1993 | Keimel | |
| 5,188,117 A | 2/1993 | Steinhaus et al. | |
| 5,228,438 A | 7/1993 | Buchanan | |
| 5,273,035 A | 12/1993 | Markowitz et al. | |
| 5,292,340 A | 3/1994 | Crosby et al. | |
| 5,318,594 A | 6/1994 | Limousin et al. | |
| 5,334,220 A | 8/1994 | Sholder | |
| 5,345,362 A | 9/1994 | Winkler | |
| 5,372,607 A | 12/1994 | Stone et al. | |
| 5,388,586 A | 2/1995 | Lee et al. | |
| 5,417,714 A | 5/1995 | Levine et al. | |
| 5,522,859 A | 6/1996 | Stroebel et al. | |
| 5,540,725 A | 7/1996 | Bornzin et al. | |
| 5,584,868 A | 12/1996 | Salo et al. | |
| 5,591,214 A | 1/1997 | Lu | |
| 5,626,623 A | 5/1997 | Kieval et al. | |
| 5,643,326 A | 7/1997 | Weiner et al. | |
| 5,674,257 A | 10/1997 | Stroebel et al. | |
| 5,697,958 A * | 12/1997 | Paul et al. | 607/31 |
| 5,725,561 A | 3/1998 | Stroebel et al. | |
| 5,741,308 A | 4/1998 | Sholder | |
| 5,814,077 A | 9/1998 | Sholder et al. | |
| 5,836,974 A | 11/1998 | Christini et al. | |
| 5,861,007 A | 1/1999 | Hess et al. | |
| 5,873,895 A | 2/1999 | Sholder et al. | |
| 5,954,755 A | 9/1999 | Casavant | |
| 5,999,850 A | 12/1999 | Dawson et al. | |
| 6,058,326 A | 5/2000 | Hess et al. | |
| 6,122,546 A | 9/2000 | Sholder et al. | |
| 6,128,529 A | 10/2000 | Esler | |
| 6,128,534 A | 10/2000 | Park et al. | |
| 6,141,586 A | 10/2000 | Mower | |
| 6,169,918 B1 | 1/2001 | Haefner et al. | |
| 6,198,968 B1 * | 3/2001 | Prutchi et al. | 607/9 |
| 6,256,541 B1 | 7/2001 | Heil et al. | |
| 6,321,115 B1 * | 11/2001 | Mouchawar et al. | 607/9 |
| 6,397,105 B1 | 5/2002 | Bouhour et al. | |
| 6,434,424 B1 | 8/2002 | Igel et al. | |
| 6,477,416 B1 | 11/2002 | Florio et al. | |
| 6,609,028 B2 | 8/2003 | Struble | |
| 6,654,637 B2 | 11/2003 | Rouw et al. | |
| 6,697,673 B1 * | 2/2004 | Lu | 607/28 |
| 6,731,980 B1 | 5/2004 | Mouchawar et al. | |
| 6,772,005 B2 | 8/2004 | Casavant et al. | |
| 6,792,307 B1 | 9/2004 | Levine et al. | |
| 6,873,875 B1 * | 3/2005 | Gilkerson et al. | 607/9 |
| 6,904,315 B2 | 6/2005 | Panken et al. | |
| 6,925,326 B1 | 8/2005 | Levine et al. | |
| 6,978,175 B1 | 12/2005 | Florio et al. | |
| 7,027,868 B2 | 4/2006 | Rueter et al. | |
| 7,123,960 B2 | 10/2006 | Ding et al. | |
| 7,130,683 B2 | 10/2006 | Casavant et al. | |
| 7,218,965 B2 | 5/2007 | Casavant et al. | |
| 7,245,966 B2 * | 7/2007 | Betzold et al. | 607/9 |
| 7,248,924 B2 | 7/2007 | Casavant | |
| 7,254,441 B2 | 8/2007 | Stroebel | |
| 7,283,872 B2 * | 10/2007 | Boute et al. | 607/8 |
| 2002/0038482 A1 * | 4/2002 | Mennicke et al. | 8/402 |
| 2002/0041700 A1 | 4/2002 | Therbaud | |
| 2002/0082646 A1 | 6/2002 | Casavant et al. | |
| 2002/0128687 A1 | 9/2002 | Baker et al. | |
| 2002/0138417 A1 | 9/2002 | Lawrence | |
| 2003/0078627 A1 | 4/2003 | Casavant et al. | |
| 2003/0083712 A1 * | 5/2003 | Rueter et al. | 607/28 |
| 2004/0010292 A1 | 1/2004 | Amblard et al. | |
| 2004/0024694 A1 | 2/2004 | Lawrence et al. | |
| 2004/0078321 A1 | 4/2004 | Lawrence | |
| 2004/0117316 A1 | 6/2004 | Gillum | |
| 2004/0143299 A1 * | 7/2004 | Casavant et al. | 607/9 |
| 2004/0158292 A1 * | 8/2004 | Sheldon et al. | 607/9 |
| 2004/0260349 A1 | 12/2004 | Stroebel | |
| 2005/0038482 A1 | 2/2005 | Yonce et al. | |
| 2005/0055059 A1 * | 3/2005 | Betzold et al. | 607/9 |
| 2005/0096708 A1 * | 5/2005 | Seim et al. | 607/28 |
| 2005/0177197 A1 | 8/2005 | Betzold | |
| 2005/0192504 A1 * | 9/2005 | Palreddy et al. | 600/509 |
| 2005/0267539 A1 * | 12/2005 | Betzold et al. | 607/9 |
| 2005/0273430 A1 | 12/2005 | Pliha | |
| 2007/0203523 A1 | 8/2007 | Betzold | |
| 2007/0213777 A1 * | 9/2007 | Betzold et al. | 607/9 |

FOREIGN PATENT DOCUMENTS

| | | |
|---|---|---|
| EP | 0 448 193 | 9/1991 |
| EP | 0624386 | 11/1994 |
| EP | 0 830 877 | 3/1998 |
| EP | 1449562 | 8/2004 |
| WO | WO95/32756 | 12/1995 |
| WO | WO02/051499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

* cited by examiner

FIG. 3

| | Noise Response Pacing Mode Options | | | |
|---|---|---|---|---|
| | AOO | VOO | DOO | Inhibit All Pacing |
| Atrium | Dependant | Reliable | Dependant | Reliable |
| Ventricle | Intact | Blocked | Blocked | Intact |

IMPLANTABLE MEDICAL DEVICE WITH ADAPTIVE OPERATION

BACKGROUND

1. Field of the Invention

The present invention relates to medical devices and more specifically to implantable medical devices.

2. Description of the Related Art

There are a variety of medical devices that sense data, provide diagnostic information, and/or deliver therapy. When such a device is implantable (in whole or in part), it is referred to as an implantable medical device (IMD). In the present application, IMD refers to devices that sense cardiac events and deliver pacing therapy. Such devices may or may not also include other functions such as defibrillation therapy (e.g., implantable cardioverter defibrillator (ICD)), other monitoring capabilities, alternate cardiac therapies, or non-cardiac monitoring and/or therapies. Thus, the term pacemaker may be used interchangeably with IMD in the present context with the understanding that either term may refer to a device with capabilities beyond those required of a pacemaker alone.

Recently, there has been a recognition that intrinsic conduction and ventricular depolarization, even if somewhat prolonged, is preferable to ventricular pacing; particularly pacing in or near the right ventricular apex. In general, this preference results from the unnatural propagation of a depolarization wavefront that is generated from such a pacing pulse (as compared to intrinsic depolarization).

Previous pacing modes tend to operate at one extreme or another. For example, in a true, single chamber AAI/R device, atrial pacing and sensing is possible, but no ability to provide ventricular pacing (or sensing) exists. On the other hand, DDD/R has historically been the default selection for dual chamber devices. The DDD/R mode will operate to maintain AV synchrony; however, the AV delay is such that intrinsic conduction is precluded in most cardiac cycles. This results in ventricular pacing in a very high percentage of cardiac cycles.

The present assignee has developed new modes that promote intrinsic conduction and are referred to herein generally as ventricular pacing protocols (VPP). Once such VPP is MANAGED VENTRICULAR PACING™ which is commercially available. A variety of VPP embodiments have previously been described for example, as in U.S. Pat. No. 6,772,005, issued Aug. 3, 2004, to Casavant et al.; U.S. application Ser. No. 10/246,816, filed Sep. 17, 2002, now U.S. Pat. No. 7,130,683 issued Oct. 31, 2006; U.S. application Ser. No. 10/755,454, filed Jan. 2, 2004, now U.S. Pat. No, 7,218,965 issued May 15, 2007; U.S. application Ser. No. 10/580,666, filed May 21, 2004, now U.S. Pat. No. 7,245,966 issued Jul. 17, 2007; U.S. application Ser. No. 11/115,605, filed Apr. 27, 2005, now U.S. Pat. No, 7,738,955 issued Jun. 15, 2010; U.S. application Ser. No. 11/096,436, filed Mar. 31, 2005, now U.S. Pat. No. 7,881,793 issued Feb. 1, 2011; U.S. application Ser. No. 10/814,692, filed Mar. 31, 2004, now U.S. Pat. No. 7,254,441 issued Aug. 7, 2007; U.S. application Ser. No. 10/971,686, filed Oct. 25, 2004, now U.S. Pat. No. 7,248,924 issued Jul. 24, 2007, where are herein incorporated by reference in their entirety.

As a generalized explanation, a VPP operates in an atrial based pacing mode to promote intrinsic conduction. Ventricular events are sensed and as long as a ventricular event is sensed in a given cardiac cycle (e.g., A-A interval) the device continues to operate in the atrial based pacing mode. This allows for ventricular sensing during the entire A-A interval. Conversely, if there is no ventricular event, the device provides a ventricular backup pace in the subsequent cycle, timed from the atrial event (paced or sensed) that initiates this cardiac cycle. Thus, in a VPP it is possible to have an entire cardiac cycle devoid of ventricular activity while ultimately maintaining AV synchrony. There are, of course, many variations and embodiments provided that are not described herein for the sake of brevity. It should be appreciated that operation in an atrial based pacing mode includes mode switching a device into such a mode (e.g. AAI/R, ADI/R) and into a mode that provides ventricular pacing or alternatively, operation in a complex mode that includes more comprehensive behavior (e.g., FIDDI).

One benefit of the VPP is that the protocol may be initiated with patients regardless of the status of their AV conduction. Those having intact or partially intact conduction will benefit in that conduction is promoted and ventricular pacing is reduced or eliminated. For those patients with heart block, the VPP will quickly move to provide ventricular pacing and periodically check to determine if conduction has returned. Both in initially recognizing the need to pace and performing the conduction checks, the methodology employed is transparent to the patient.

As previously indicated physicians implanting a dual chamber device often utilize nominal settings and program the device to DDD/R due to its simplicity. The VPP allows for the same type of comprehensive reliability across patient profiles and without the need to program numerous parameters upon implant. The VPPs are preferable in that that they reduce or minimize ventricular pacing when intact conduction is present.

BRIEF DESCRIPTION OF THE DRAWINGS

FIG. 3 is a table indicating response taken to noise based upon classification.

DETAILED DESCRIPTION

Figure 1:
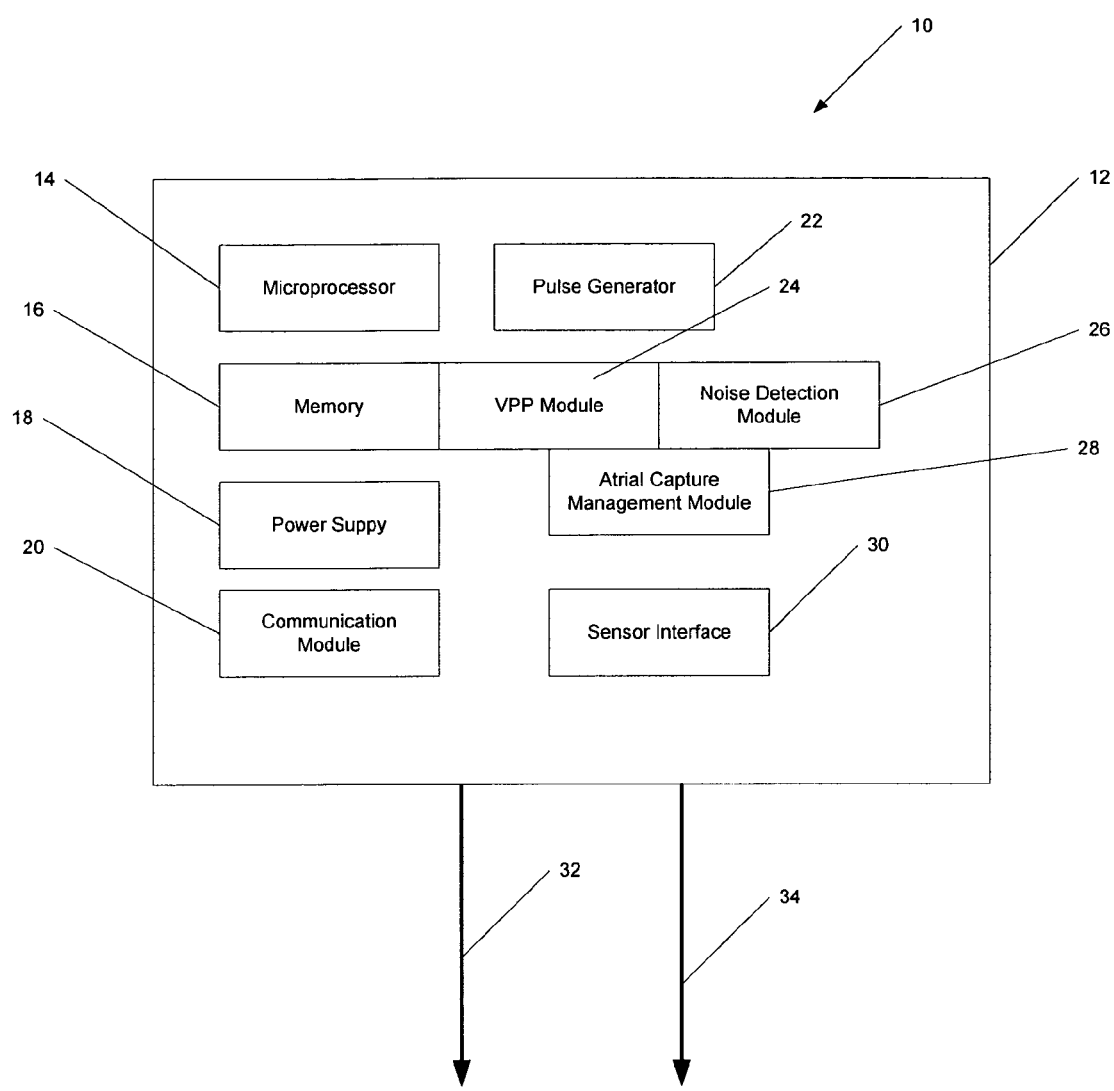
FIG. 1 is a schematic diagram illustrating an implantable medical device.

FIG. 1 is a schematic illustration of an implantable medical device (IMD) 10 having pacing capabilities. While not illustrated, IMD 10 may also include a variety of other monitoring, diagnostic and therapeutic functions. Further, FIG. 1 is not meant to comprehensively illustrate all components of an implantable pacemaker.

The IMD 10 includes a housing 12 that contains a microprocessor 14, memory 16, a power supply (e.g., battery) 18, a communication module 20 that facilitates telemetry to an external device and a pulse generator 22 for generating pacing pulses. A sensor interface 30 is provided to collect data from one or more sensors/electrodes, one or more of which may be disposed on leads 32, 34. The pacing stimuli generated by the pulse generator 22 is deliverable via the leads 32, 34. Also illustrated in FIG. 1 are a VPP module 24, noise detection module 26 and atrial capture management module 28. It should be appreciated that these functions may be algorithms stored in the memory 16 or incorporated into other hardware, software, or firmware.

In operation, the IMD 10 senses cardiac events and provides an appropriate response. Most typically, cardiac events are sensed via electrodes on the leads 32, 34. These electrodes pick up electrical signals indicative of specific activities within the heart, typically represented as an electrogram (EGM) within the device or an electrocardiogram (ECG) when based upon surface collected data. As is well known, the cardiac cycle includes an atrial depolarization represented electrically by a P wave, ventricular depolarization represented by the QRS complex, and repolarization represented by a T wave. While sensing algorithms can be relatively complex, in general a sensed P wave indicates intrinsic atrial depolarization while a sensed R wave indicates intrinsic ventricular depolarization. For a given pacing mode, if a P wave or R wave is not sensed within a predetermined time frame, then the IMD 10 will provide atrial or ventricular pacing with appropriate timing. There are numerous variations to this generalization such as overdrive pacing or various tachycardia pacing therapies. The main point herein is that the IMD 10 senses data and responds in some fashion to that data.

Though the IMD 10 is implanted within the patient and includes shielding and various design advancements, it is not immune from electromagnetic interference (EMI) or other types of noise. Common sources of noise would include physical contact with certain household appliances, vending machines, contact with ungrounded electrical devices (e.g., swimming pool lights), exposure to certain tracking/security devices, and exposure to medical testing such as an MRI field. Generally, noise resulting from such exposure is minimal and transient.

Furthermore, the IMD 10 includes the noise detection module 26 to identify the presence of noise. Thus, when noise is detected the IMD 10 will modify its behavior. Each device may take distinct action and each action may depend upon the specific noise and/or environment.

As a generalization, the IMD 10 will not consider signals received as valid cardiac indicators when noise is detected. As such, the IMD 10 is unable to pace (or otherwise act) in response to sensed signals during this noise window, since no sensed signal may be deemed reliable. Noise exposure is typically of a short duration; however, the IMD 10 has no way to determine how long it will last. Thus, the previous response to noise has been to provide asynchronous pacing during periods of noise. For example, assume a given patient has a right ventricular lead implanted. When noise is present, the IMD 10 will provide ventricular pacing pulses based upon the best available information (e.g., what rate to pace at, last paced or sensed event) but unsynchronized with respect to any intrinsic atrial or ventricular activity actually occurring. This response is typically provided regardless of the therapy being delivered. That is, if pacing is permitted it will be provided during the duration of the noise. In dual chamber devices, this asynchronous pacing is provided in both the atrium and ventricle. This dual chamber pacing will be coordinated (i.e., a pace followed by an appropriate AVI with a V pace) but is asynchronous with respect to the intrinsic events of the heart or any event that otherwise would be sensed absent noise).

Figure 2:
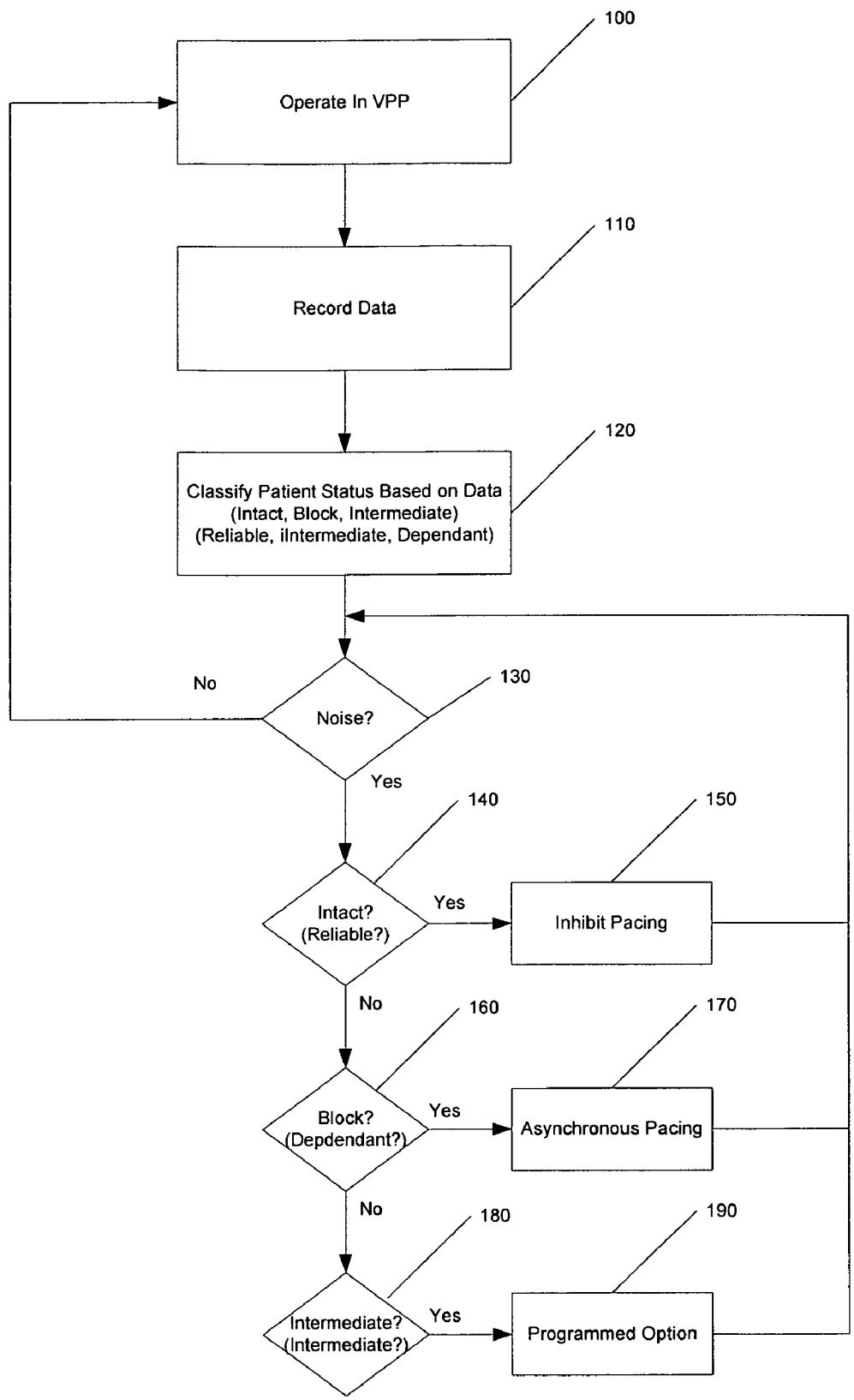
FIG. 2 is a flowchart describing one method of selecting a noise response.

FIG. 2 illustrates a noise response of the IMD 10 according to the present invention. The IMD 10 operates (100) in a Ventricular Pacing Protocol (VPP), such as MVP™. As indicated, the VPP is a mode or mode switching module that promotes intrinsic conduction and maintains AV synchrony. A full cardiac cycle is permitted to elapse without ventricular pacing and a ventricular sense occurring within this window maintains operation in this state (deemed to be in an atrial based mode). If a full cycle elapses without a ventricular sensed event, a ventricular pace is delivered at an appropriate time in the immediately subsequent cardiac cycle (deemed to be a dual chamber based mode). There are number embodiments of VPPs and how they respond subsequently. In some such embodiments, the device reverts to the atrial based mode after one cycle with a ventricular pace. Then, if a certain condition is met, the IMD 10 operates in a DDD/R mode for a particular period of time. Such a condition might be if 2 of 4 consecutive cycles lack intrinsic conduction. Once in the DDD/R mode, the IMD 10 will periodically perform a conduction check to determine if intrinsic conduction has returned. The initial conduction check occurs a short time after entering the mode, e.g., after 1 minute in DDD/R. Subsequent checks (assuming each is unsuccessful) occur after progressively longer durations (e.g., 2, 4, 8, 12, 24, 48 minutes, 1, 2, 4, 8 hours etc.). At some point, a longest duration is reached (e.g., 16 or 17 hours) between conduction checks. This assures that a conduction check is performed once per day but at different times of the day. Each conduction check is brief (one to a few cardiac cycles) and is generally unnoticeable to the patient. This permits the VPP to be utilized on any patient; even those with complete heart block. Conversely, when any conduction check is successful, the IMD 10 operates in the atrial based pacing mode and significantly reduces the occurrence of ventricular pacing, as compared to operation in, e.g., DDD/R over the same time period.

During operation of the IMD 10 the device records (110) data. One parameter recorded will relate to the amount of operation in the atrial based mode as compared to the dual chamber mode and/or operation in DDD/R or a similar traditional mode. The particular type of data may vary. For example, the IMD 10 may record a percentage of total time operated in the atrial based mode, a number of cardiac cycles, a percentage of total cycles operated in the atrial base mode, the number/percentage of ventricular pacing pulses delivered over a given time period or number of cycles, or some suitable alternative.

Based upon this data, the IMD 10 classifies (120) the patient status. For purposes of this description, the patient will be classified as having generally intact conduction (intact), complete or almost complete block (blocked), or intermediate. It should be appreciated that there are medical classifications/definitions of AV conduction and the terms (intact, blocked, intermediate) are not meant to be defined herein by such medical definitions. The parameters used to define these three categories may be set by the manufacturer or may be selectively programmed. In practice, the vast majority of patients will be at one end of the spectrum or the other. That is, there is either a very low occurrence of ventricular pacing or a very high occurrence. In one embodiment, providing ventricular pacing in 20% or less of the relevant cardiac cycles is labeled as intact, 20%-80% is labeled intermediate and 80% or greater is labeled blocked. In another embodiment, these values are 10%, 10%-90%, and 90% or greater. In yet another embodiment, the patient is labeled intact if pacing occurs in less than 5% and labeled blocked using either of the two upper limits. Again, the parameters may be programmed to any value specified. The intermediate category may also be eliminated, with the patient defined as either intact or blocked.

It should be appreciated that similar data recording and classification may be provided for atrial pacing. That is, with a dual chamber device having atrial pacing capability, the device may provide atrial pacing frequently or infrequently, depending upon need. By relying upon the SA node to initiate pacing (when appropriate), the pacing rate is directly controlled by physiological conditions as opposed to electromechanical surrogates (e.g., an accelerometer). For atrial pacing, the classifications would be reliable, intermediate (optional), dependant. Reliable would indicate that an intrinsic sinus rhythm is present in an appropriate percentage of cycles. Dependant would indicate that the patient relies upon atrial pacing in a large percentage of cardiac cycles and intermediate, if used would be the values between. The actual time or percentages used may be the same as those identified for ventricular classifications, or may be set independently and vary.

As operation continues with the VPP, sufficient data is collected to classify the patient. In addition, the noise detection module 26 functions and monitors (130) for noise. If no noise is detected (130), normal operation continues (100). If noise is detected (130), then the next action taken will depend upon the classification made in step 120. Assuming the patient is labeled as intact (based upon data collected during operation of the VPP), then the IMD 10 will inhibit pacing, due to the previously recorded success of the VPP. This means that ventricular pacing will not be provided asynchronously, as was a default in previous devices during noise situations. During this period of noise, the IMD 10 is unable to accurately sense intrinsic ventricular activity. As indicated, the duration of the noise is typically short and thus, this poses little risk to the patient. The benefit is that no unnecessary ventricular pacing is provided.

Conversely, if the patient is labeled as blocked (160), then asynchronous pacing (170) is provided. It should be appreciated that a patient labeled as blocked may have their IMD 10 operate in DDD/R mode a substantial period of the time. Thus, the noise response is consistent with that in the DDD/R mode. Alternatively, a patient labeled as blocked (e.g., requiring ventricular pacing 85% of the time) may be operating in an atrial based mode (hence ventricular pacing is not required) at the time noise is detected. Asynchronous pacing (170) is still provided due to the high likelihood of a need for ventricular pacing when the device is unable to accurately sense.

As previously indicated, most patients will have data at one extreme or the other making classification relatively easy. Those patients within the definable margins are likewise reliably classified. Those who are classified as intermediate (e.g., 20%-80% ventricular pacing) will be rare but pose a greater challenge. The indicated response for intermediate patients in the presence of noise is to follow the programmed option 190. Thus, the physician or caregiver may program the desired action (e.g., whether or not to provide asynchronous pacing during noise) for intermediate classifications. A conservative default may be to treat intermediate patients as blocked (effectively removing this as a classification and expanding the range of what is considered blocked). Alternatively, further subclassifications may be provided, e.g., when ventricular pacing is occurring in 20%-40% treat the intermediate classification as intact. Another variable may be recent trend data. For example, overall a patient may have ventricular pacing 30% of the time; however, in the last four hours, the percentage has been less than 10%. Thus, that provides a basis to inhibit asynchronous pacing (150) rather than pace for this intermediate patient. Another alternative used alone or in combination is to treat certain intermediate patients as intact for a limited amount of time. For example, if the noise duration extends for longer than X seconds or Y cardiac cycles, then the intermediate classification is considered to be block. As should be appreciated, the time frames and requirements for these types of sub-classifications may vary dramatically and could be programmed with specificity.

During the duration of the noise, the appropriate action is taken (150, 170, 190). When noise is no longer an issue (130), the process returns to normal operation in the VPP 100.

The atrial classifications are indicated in parenthesis in FIG. 2. It should be appreciated that the atrial and ventricular classifications are separate and distinct. That is, a given patient may have intact AV conduction (as used herein) but may be classified as dependent for atrial pacing. Thus, the flowchart of FIG. 2 illustrates two separate processes that are presented together for brevity and clarity.

FIG. 3 is a table that sets out the various conditions and responses for the atrial and ventricular responses, based upon classification according to the present invention. As indicated, when the atrial chamber (or atrium) is classified as dependant and the ventricular chamber is classified as intact, the response during noise is to operate in an AOO mode. That is, asynchronous pacing is provided in the atrium but inhibited in the ventricle. When the atrial chamber is reliable and the ventricular chamber is blocked, the noise response is to operate in VOO. That is, atrial asynchronous pacing is inhibited and ventricular asynchronous pacing is provided. Finally, when the atrial chamber is dependant and the ventricular chamber is blocked, the noise response is operation in a DOO mode where asynchronous pacing is provided in both the atrium and ventricle.

There are various sources and types of noise that a patient may encounter. Through shielding, circuit design, and various noise algorithms, the vast majority of this noise will not interfere with normal operation of the IMD 10. That is, merely because the patient is in a noisy environment does not mean that the IMD 10 will be affected by that noise. It is only when the IMD 10 is actually affected by noise and recognizes the same that these responses are taken. Most types of noise will have a short duration, as explained previously. Some types of noise will have an expected longer duration.

One example of noise having an expected longer duration is the field generated during an MRI. The MRI field may have a variety of effects on the IMD 10 beyond generating noise that precludes accurate sensing. For example, currents may be induced in some leads that result in either a stimulation of the patient, a pulse directed towards the circuitry, and/or heating of the components and hence the surrounding tissue. Thus, noise detection module 26 may include a specific MRI detection module (not separately shown) to identify that the IMD 10 is in an MRI field. A variety of methods to detect the MRI field are known, such as sensing the presence of a strong magnetic field.

With previous devices, the patient would have their IMD 10 programmed to an MRI safe setting some time prior to a scheduled MRI. This may require operation in this setting for many days or even weeks as scheduling may be difficult. Thus, if the VPP is disabled in anticipation of an MRI, that patient loses the benefit provided by a reduction in pacing over that time period. Of course, there may be a similar delay following the MRI before the patient may have the device programmed to the previous settings. This results from the fact that in most MRI settings, neither the equipment nor the proper medical practitioners are readily available to program the device. In an emergency setting, the MRI may be administered without knowledge of the device, with knowledge of the device and a calculation of the risk, or the MRI may be delayed until the IMD 10 is programmed to an MRI safe setting.

The present invention functions as described above, even when MRI is the known source of the detected noise. This provides a benefit to the patient in that the VPP operates up until and right after the MRI session, thereby reducing pacing over a longer duration. For those patients that require asynchronous pacing, this is again only provided over the duration required. In both cases, this reduces patient burden (in scheduling multiple appointments), avoids potential errors/oversights, and reduces clinician burden in reducing office visits that only occur for MRI programming.

Figure 4:
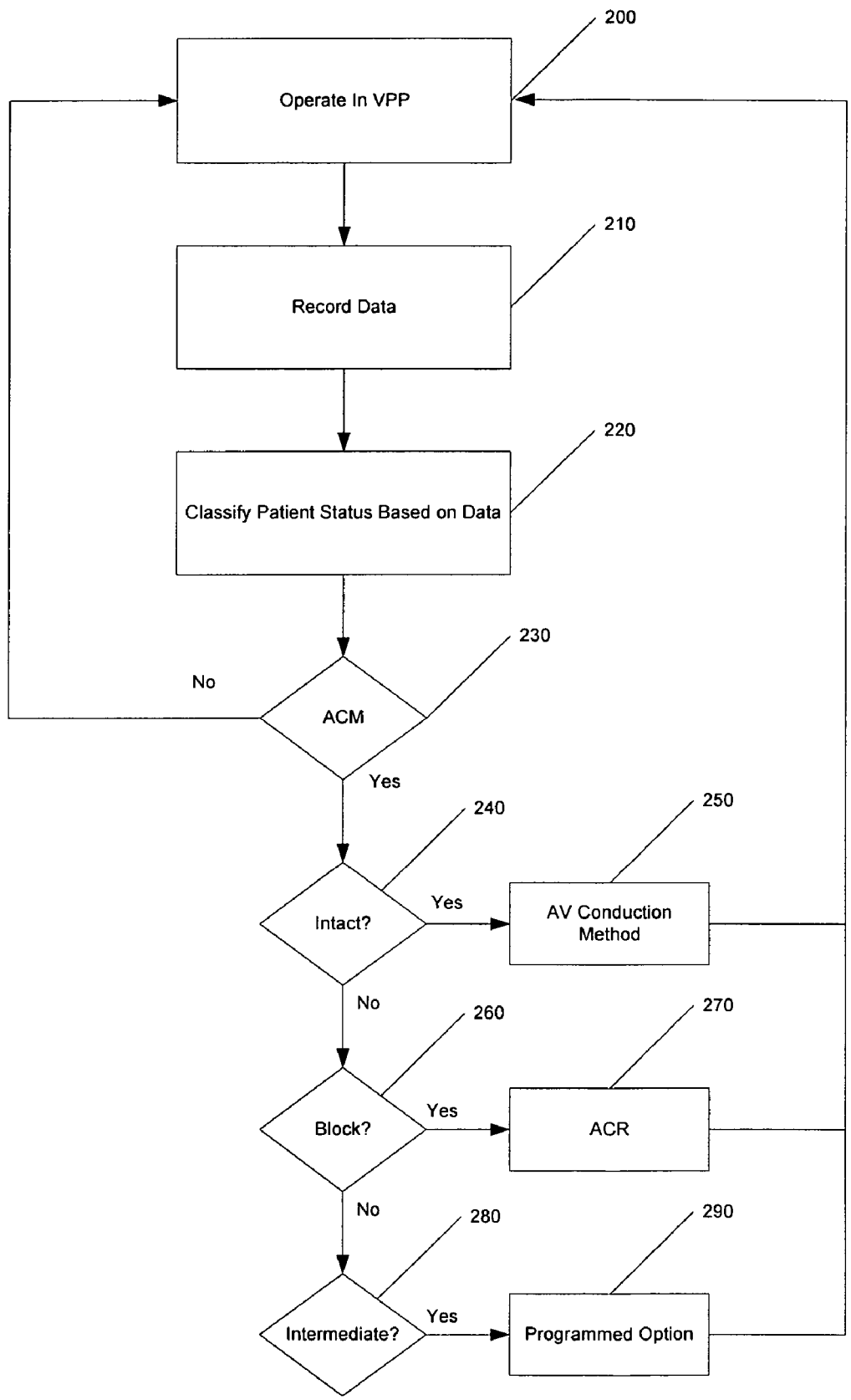
FIG. 4 is a flowchart describing one method of selecting a threshold measurement algorithm.

FIG. 4 is a flowchart illustrating a process for identifying an appropriate atrial capture management method. The IMD 10 operates 200 according to the VPP, such as for example, the MVP™ mode. As described above, the IMD 10 records (210) data and classifies (220) the patient status. At various times, the IMD 10 will perform threshold testing to determine the proper thresholds for pacing. The goal is to determine the appropriate pacing pulse levels (e.g., magnitude, duration) to assure capture (with a safety margin in some cases) while minimizing power consumption. When done for atrial pacing, this is referred to as atrial capture management (ACM) and may take two forms. The first is referred to as the AV conduction method. Here, an atrial pace is delivered knowing, in advance, that AV conduction is intact. The ventricular channel is monitored and if ventricular depolarization occurs within an expected interval following the atrial pace, the atrial pace is determined to have captured. If the ventricular event fails to occur or occurs outside this window (underlying ventricular rate or intrinsic atrial event occurs after the pace), then the atrial pace is determined to be below threshold and hence did not capture the atrium. Levels are adjusted and this test is repeated until capture is reliably determined.

The other method of ACM is referred to as atrial chamber reset (ACR). This is used when AV conduction is not reliable or complete block is present. In this method, atrial timing is monitored. Prior to an expected atrial event (e.g., based on rate), an atrial pacing pulse is delivered. If this pulse captures the atrium, then the expected atrial event is inhibited. Conversely, if the atrial pacing pulse fails to capture, the expected atrial event occurs. This method is somewhat more difficult to conduct as pacing and sensing occur on the same channel. Furthermore, this necessitates at least a minor change in timing due to the early delivery of atrial pacing pulses.

Thus, with the VPP in operation, the IMD 10 determines the type of ACM to employ (230) based upon the determined classification. If the patient is intact (240), then the AV conduction method (250) is utilized. In order to be classified as intact, the patient must have intrinsic AV conduction in a large percentage of cardiac cycles; thus, conduction is reliable and this type of ACM may be performed (the specific values employed may be the same as the determination f for noise purposes, as previously discussed, or programmed to different values). As indicated, this type of ACM is preferable in that it does not deliver early atrial pacing pulse and monitors for capture on a separate channel from that delivering pacing. The present invention provides a relatively simple automated mechanism to determine which methodology to employ. As an example, a patient having a previous device operating in DDD/R may have completely intact conduction; however, the DDD/R mode virtually assures ventricular pacing and makes a determination of AV conduction rather difficult.

Conversely, when classified as blocked (260), the IMD 10 will perform ACM using (270) the ACR method. This method is selected because this classification of patient does not have sufficiently reliably AV conduction to facilitate the AV conduction method of ACM. Thus, while the AV conduction method is preferable to ACR, ACR is preferable to not performing conduction check and can be successfully used to determine thresholds.

Again, the intermediate classification (280) is unlikely; however, the type of ACM employed may be a programmable option (290). The same types of variations discussed above with respect to noise are applicable here. Certainly patients near the threshold values for intact classifications may benefit from an attempt to utilize the AV conduction method. In another embodiment, an attempt is made to utilize the AV conduction method for all intermediate patients. If successful, then this method is used again. If unsuccessful, ACR is utilized and becomes the default until or unless the patient classification changes.

The invention claimed is:

1. A method comprising:
   operating an implantable medical device (IMD) having pacing capabilities according to a Ventricular Pacing Protocol (VPP);
   monitoring performance of the IMD including frequency of occurrence of ventricular pacing while operating according to the VPP;
   classifying an AV conduction status based upon the performance of the IMD while operating according to the VPP, wherein the conduction status is given a first classification or a second classification responsive to the monitored frequency of occurrence of ventricular pacing and wherein the frequency of occurrence of ventricular pacing is lower for the first classification than for the second classification;
   determining presence of a condition allowing for selection of a first response or a second response; and
   responsive to the presence of the condition, selecting the first response when the AV conduction status has been given the first classification and selecting the second response when the AV conduction status has been given the second classification.

2. The method of claim 1, further comprising:
   recording data within a memory of the IDM indicative of ventricular pacing during operation according to the VPP, wherein classifying the AV conduction status occurs based upon the recorded data.

3. The method of claim 1, wherein the condition is presence of noise detected by the IDM.

4. The method of claim 3, wherein the first response is inhibition of pacing and the second response is delivering asynchronous pacing.

5. The method of claim 4, wherein the first classification is given responsive to occurrence of ventricular pacing in 10% or less of a total number of cardiac cycles operated according to the VPP.

6. The method of claim 4, wherein the first classification is given responsive to occurrence of ventricular pacing in 20% or less of a total number of cardiac cycles operated according to the VPP.

7. The method of claim 1, wherein the condition is the selective performance of an atrial capture management (ACM) test.

8. The method of claim 7, wherein the first response is performing ACM utilizing AV conduction methodology and the second response is performing ACM using an atrial chamber reset (ACR) methodology.

9. The method of claim 8, wherein the first classification is given responsive to occurrence of ventricular pacing in 10% or less of a total number of cardiac cycles operated according to the VPP.

10. The method of claim 8, wherein the first classification is given responsive to occurrence of ventricular pacing in 20% or less of a total number of cardiac cycles operated according to the VPP.

11. A method comprising:
    operating an implantable medical device (IMD) according to a Ventricular Pacing Protocol (VPP) wherein the IMD operates in an atrial based pacing mode and monitors for intrinsic AV conduction over an entire cardiac cycle and provides ventricular backup pacing in a cardiac cycle subsequent to a first cardiac cycle devoid of sensed ventricular activity;

monitoring the operation of the IMD during operation according to the VPP and recording data indicative of frequency of occurrence of ventricular pacing;

classifying an AV conduction status to a first or a second status based upon the data, wherein the first status is indicative of a lower frequency of occurrence of ventricular pacing than the second status;

monitoring for the presence of noise;

providing asynchronous pacing if noise is detected and the AV Conduction status is classified as the second status; and inhibiting asynchronous pacing if noise is detected and the AV conduction status is classified as the first status.

* * * * *